(12) United States Patent
Ainslie et al.

(10) Patent No.: US 9,901,569 B2
(45) Date of Patent: Feb. 27, 2018

(54) COMPOSITIONS AND METHODS FOR INHIBITING LEISHMANIA

(71) Applicant: OHIO STATE INNOVATION FOUNDATION, Columbus, OH (US)

(72) Inventors: Kristy Ainslie, Chapel Hill, NC (US); Eric Bachelder, Chapel Hill, NC (US); Shalini Gautam, Aligarh (IN); Kevin Peine, Chardon, OH (US); Abhay Satoskar, Upper Arlington, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 14/924,605

(22) Filed: Oct. 27, 2015

(65) Prior Publication Data
US 2016/0120844 A1     May 5, 2016

Related U.S. Application Data

(60) Provisional application No. 62/072,634, filed on Oct. 30, 2014.

(51) Int. Cl.
| A61K 31/415 | (2006.01) |
| A61K 31/7048 | (2006.01) |
| A61K 45/06 | (2006.01) |

(52) U.S. Cl.
CPC ........ *A61K 31/415* (2013.01); *A61K 31/7048* (2013.01); *A61K 45/06* (2013.01)

(58) Field of Classification Search
CPC .. A61K 45/06; A61K 31/7048; A61K 31/415; A61K 2300/00
USPC .................................................. 514/31, 406
See application file for complete search history.

(56) References Cited

U.S. PATENT DOCUMENTS

| 7,576,116 B2 | 8/2009 | Chen |
| 8,039,502 B2 | 10/2011 | Chen et al. |
| 8,080,574 B2 | 12/2011 | Chen |
| 8,541,460 B2 | 9/2013 | Chen |
| 8,546,441 B2 | 10/2013 | Chen |

OTHER PUBLICATIONS

Chiu et al., Eradication of Intracellular *Salmonella enterica* Serovar Typhimurium with a Small-Molecule, Host Cell-Directed Agent. Antimicrobial Agents and Chemotherapy, Dec. 2009, vol. 53, No. 2, p. 5236-5244.*
Santa-Rita et al., Effect of the lysophospholipid analogues edelfosine, ilmofosine and miltefosine against Leishmania amazonensis. Journal of Antimicrobial Chemotherapy (2004) 54, 704-710.*
Bachelder, et al., "A cetal-derivatized dextran: an acid-responsive biodegradable material for therapeutic applications", J Am Chem Soc, 2008, vol. 130, No. 32, pp. 10494-10495.
Peine, et al., "Liposomal resiquimod for the treatment of Leishmania donovani infection", J Antimicrob Chemother, 2014, vol. 69, pp. 168-175.
Van der Vaart, et al., The DNA Damage-Regulated Autophagy Modulator DRAM1 Links Mycobacterial Recognition via TLR-MYD88 to Autophagic Defence, Cell Host & Microbe, vol. 15, Issue 6, p. 755 (Jun. 2014).

* cited by examiner

*Primary Examiner* — Yih-Horng Shiao
(74) *Attorney, Agent, or Firm* — VLP Law Group, LLP; Jeremy A. Cubert, Esq.

(57) ABSTRACT

Compositions and methods for inhibiting Leishmaniasis using AIs are provided. Aspects provide compositions and methods for administering AIs alone or in combination with other compounds to infected hosts.

6 Claims, 8 Drawing Sheets

COMPOSITIONS AND METHODS FOR INHIBITING LEISHMANIA

PRIORITY CLAIM

This application claims priority to U.S. Provisional Patent Application Ser. No. 62/072,634 filed on Oct. 30, 2014. The above referenced application is incorporated herein by reference as if restated in full. All references cited herein, including, but not limited to patents and patent applications, are incorporated by reference in their entirety.

BACKGROUND

Leishmaniasis is a protozoal parasitic disease transmitted by sandflies and found in the tropics, subtropics, and southern Europe. The most common forms of the leishmaniasis are cutaneous (skin) and visceral (organs including spleen, liver, and bone marrow). The disease affects millions of people worldwide. Sandflies carrying the promastigote form of the parasite bite a human host, attracting macrophages to the site of the wound. Promastigotes are then phagocytized by the macrophages, transform into amastigotes and multiply within the macrophage and various species-specific tissues. Sandflies are infected by amastigotes during feeding, and the amastigotes transform into the promastigote form in the sandfly gut, continuing the infection cycle.

Current treatments for leishmaniasis include sodium stibogluconate (SSG), amphotericin B (conventional and lipid formulations), pentamidine isethionate, miltefosine, ketoconazole, itraconazole, and fluconazole. However, these therapies result in significant side effects. Side effects of SSG treatment, for example, include phlebotoxicity and pancreatitis. Amphotericin B's side effects include high fever, shaking chills, hypotension, anorexia, nausea, vomiting, headache, dyspnea and tachypnea, drowsiness, and generalized weakness. Thus, new therapies that can replace or reduce the dose of conventional therapies are desirable.

SUMMARY

Aspects described herein provide compositions and methods for inhibiting *Leishmania*. In one aspect, the growth of *Leishmania* is inhibited by providing or administering the following compound to a cell infected with *Leishmania* spp.

Formula I

In yet another aspect, compositions for inhibiting Leishmaniasis are provided, comprising the compound of Formula I and another compound (e.g., SSG, amphotericin B, pentamidine isethionate, miltefosine, ketoconazole, itraconazole, and fluconazole).

Further aspects include methods of treating Leishmaniasis comprising administering a composition comprising the compound of Formula I to a mammal in need of treatment wherein parasite burden is reduced to less than about 47% of the untreated control. In another aspect, the compound is AR-12. In yet another aspect, the compound of Formula and another compound (e.g., SSG, amphotericin B, pentamidine isethionate, miltefosine, ketoconazole, itraconazole, or fluconazole) is administered to the patient resulting parasite burden is less than about 1% of the untreated control.

BRIEF DESCRIPTION OF THE DRAWINGS

The feature and nature of the present disclosure will become more apparent from the detailed description set forth below when taken in conjunction with the accompanying drawings.

DETAILED DESCRIPTION

The disclosed methods, compositions, and devices below may be described both generally as well as specifically. It should be noted that when the description is specific to an aspect, that aspect should in no way limit the scope of the methods. Articles and patents cited herein are hereby incorporated by reference in their entirety.

Aspects provide methods of reducing the LDU (Leishman Donovan Units of *Leishmania* in a host by administering an autophagy inducer and multi-targeted kinase inhibitor ("AI") to the host wherein the titer of Leishmaniasis is reduced. In another aspect, the LDU of *Leishmania* in the host is reduced to less than 47% of the untreated control. In another aspect, the AI is AR-12. In a further aspect, the host is a mammal (e.g., human).

In yet another aspect, the AI is co-administered with a second compound. The second compound can be selected from, for example, SSG, amphotericin B, pentamidine isethionate, miltefosine, ketoconazole, itraconazole, or fluconazole.

Further aspects provide methods of treating a host infected with Leishmaniasis, by administering a daily or more frequent dose of at least about 0.1 mg/kg of an AI and a second compound to the host. In one aspect, the AI is AR-12.

In yet another aspect, the second compound is selected from the group consisting of SSG, amphotericin B, pentamidine isethionate, miltefosine, ketoconazole, itraconazole, and fluconazole.

Aspects provide compositions comprising an AI, amphotericin B, and a pharmaceutically acceptable carrier (e.g., liposome and micelle). Other aspects provide compositions comprising an AI, SSG, and a pharmaceutically acceptable carrier (e.g., liposome, micelle, and colloidal suspension). In yet another aspect, the AI is AR-12.

Aspects described herein provide compositions and methods for inhibiting the growth of, interfering with the life cycle of, and preventing transmission of the protozoan parasites of the genus *Leishmania* which cause the disease Leishmaniasis in mammals. Aspects provide compositions comprising AIs, including AR-12, as described herein alone and in combination with other therapeutic modalities (e.g., SSG, amphotericin B, pentamidine isethionate, miltefosine, ketoconazole, itraconazole, and fluconazole). Compositions described herein can be administered to a mammal in need of treatment by any conventional route of administration including injection (intravascular, intramuscular, subcutaneous, and intradermal), oral, topical, inhalational, intranasal, rectal, and vaginal). The term "administer" or "administration" also refers to a medical professional providing or prescribing the compositions described herein to the patient.

In one aspect, AIs suitable for use herein include, for example, the compounds described in U.S. Pat. Nos. 7,576,116, 8,546,441, 8,541,460, 8,039,502, and 8,080,574 hereby incorporated by reference in their entirety ("AIs"). In another aspect, the AI is AR-12 ($C_{26}H_{19}F_3N_4O$ and 2-amino-N-(4-(5-(phenanthren-2-yl)-3-(trifluoromethyl)-1H-pyrazol-1-y)phenyl)acetamide)), having the following structure:

Formula I

AR-12 is a small-molecule autophagy inducer and multikinase inhibitor that was derived from structural modifications of the cyclooxygenase-2 (Cox-2) inhibitor, celecoxib, but does not possess COX-2 inhibitory activity. The compositions for use in the invention also comprise nanoparticle or microparticle formulations (e.g., acetalated dextran microparticles, and liposomes). Other suitable biodegradable polymers include, but are not limited to PLGA, PCL, PBAE, PLA, and PGA. The nanoparticle or microparticles can be formed through any suitable mechanism known in the art (e.g., ethanol injection, emulsion chemistry, and coacervation).

AR-12 concentrations can be limited for in vivo application because of the drug's hydrophobicity. To overcome solubility issues, AR-12 can be provided in particles (e.g. liposomes, and polymeric microparticles) that can passively target the host cell. Acid sensitive polymers can be used to release drug in the phagocyte's phagosome, due to the lower pH in this environment.

In one aspect, an AI (e.g., AR-12) can be encapsulated into particles, with the potential for injection (e.g., i.v., i.p) or non- parenteral delivery, respectively. See Bachelder, E. M. Beaudette, T. T. Broaders, K. E.; Dashe, J. Frechet, J. M., Acetal-derivatized dextran: an acid-responsive biodegradable material for therapeutic applications. *J Am Chem Soc* 2008, 130 (32), 10494-5 incorporated in its entirety herein. See also, Peine et al., Liposomal resiquimod for the treatment of *Leishmania donovani* infection, J Antimicrob Chemother 2014; 69: 168-175.

In another aspect, polymeric particles can be made through single emulsion chemistry. Ac-DEX PMPs can be fabricated through double emulsion chemistry. An initial phase of PBS can be homogenized with an organic phase containing AR-12 and Ac-DEX. In another aspect, the remaining emulsion steps can follow the same synthesis steps as with a single emulsion.

Figure 1:
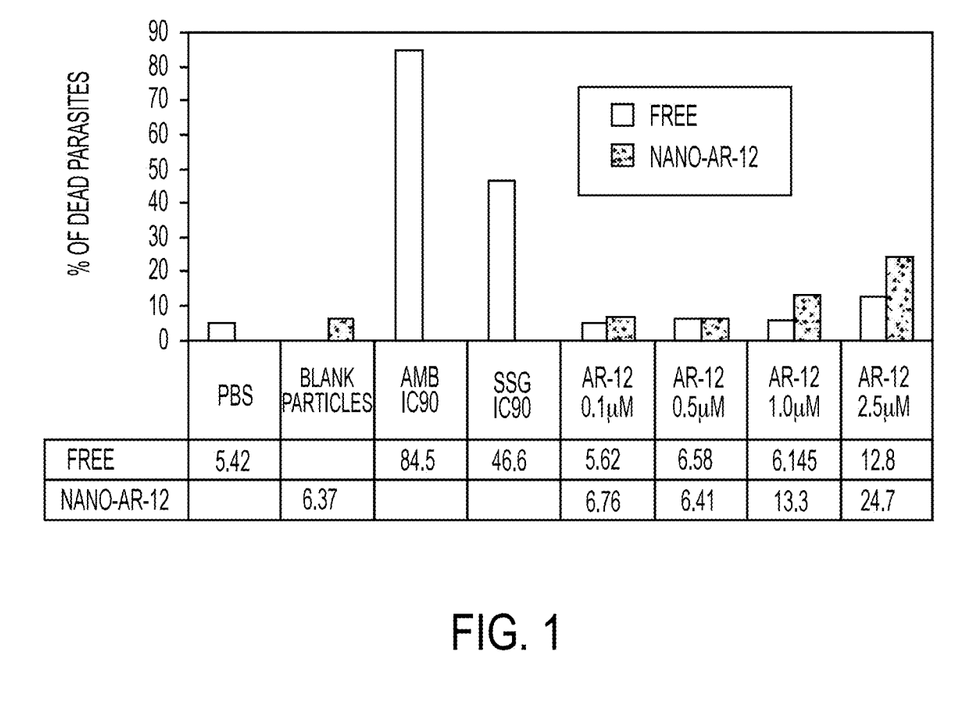
FIG. 1 shows the exemplary effects of AR-12 directly against the *Leishmania donovani* promastigote.

As shown in FIG. 1, fluorescently dsRED labeled *L. donovani* promastigotes were incubated with increasing concentrations of AR-12 or controls for 72 hours. Promastigote inhibition was evaluated via high-throughput flow cytometery imaging. Saponin was used a positive control. Increasing concentrations of nanoparticle encapsulated AR-12 above 0.5 μM and free AR-12 above 1.0 μM increased the percentage of promastigotes killed. For example, increasing nanoparticle encapsulated AR-12 from 0.5 μM to 1.0 μM increased the percentage of dead parasites by about 50% (from about 5% to about 10%). Increasing nanoparticle encapsulated AR-12 from 1.0 μM to 2.5 μM increased the percentage of dead parasite by about another 50% (from about 10% to about 20%).

Figure 2:
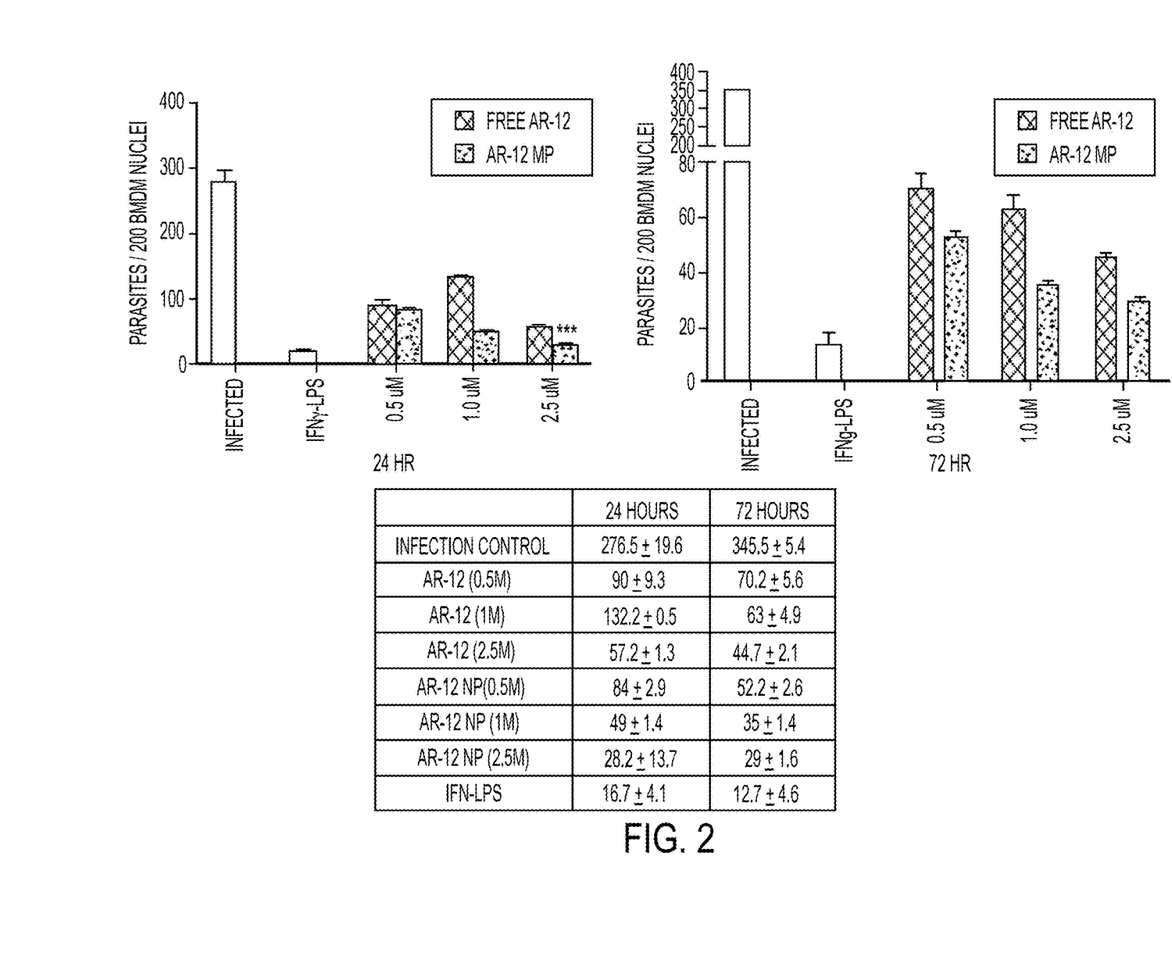
FIG. 2 shows the results of an exemplary treatment of infected macrophages with AR-12.

As shown in FIG. 2, *L. donovani* amastigotes were used to infect primary mouse derieved macrophage (BMDMs) at an MOI (multiplicity of infection) of 1:7. Three individual cultures for each group were analyzed via light microscopy after after 24 and 72 hour in culture. The number of parasites can be compared to untreated (infected) and those treated with the positive control interferon-gamma (IFNg) and lippoolyscahride (LPS). Macrophages treated with nanoparticle encapsulated AR-12 had less than half the number of parasites compared to free AR-12 treated macrophages at a 1.0 μM concentration and a little more than half the number of parasites after 72 hours.

Figure 3:
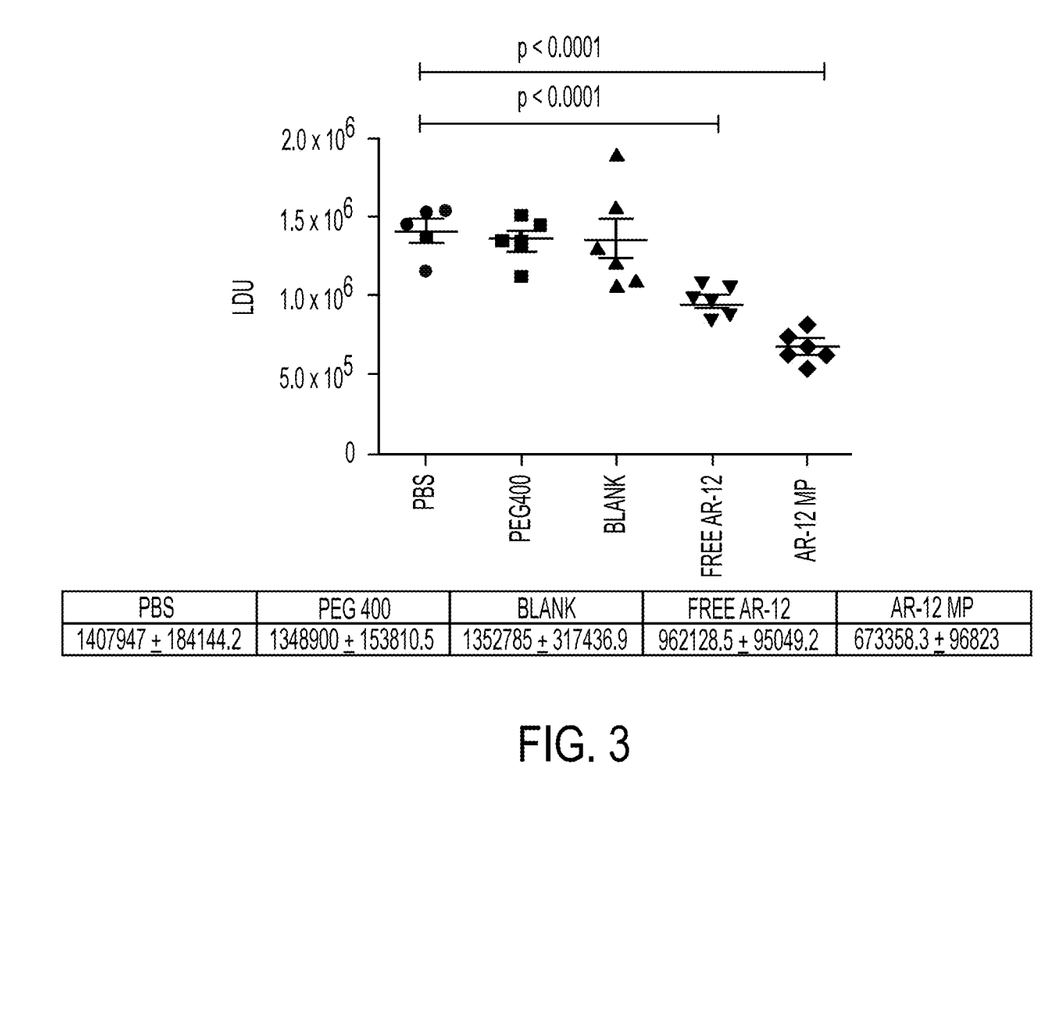
FIG. 3 shows an exemplary in vivo evaluation of AR-12 as a treatment for a mouse model of Leishmaniasis by observing parasite load in the mouse liver.

FIG. 3 provides an exemplary in vivo evaluation of AR-12 in the liver. BALB/c mice were infected with $1\times10^7$ amastigotes by tail vein injections and mice were given PBS, AR-12 in a PEG-400/Ethanol solution, blank Ace-DEX nanoparticles, unencapsulated AR-12, or AR-12 in Ace-DEX nanoparticles at day 14 and day 21 post infection. AR-12 was given at 6.4 μg/mg (38.4 μg /mouse). Mice were sacrificed at Day 28 (7 days post 2nd treatment) and parasite load was analyzed via histology and light microscopy for Leishman-Donovan units (LDU) which represents amastigote number per 1,000 host cell nuclei ×organ weight (in grams) (n=5). Treatment with free AR-12 and encapsulated AR-12 decreased LDU by 1.4 fold and 2 fold respectively.

Figure 4:
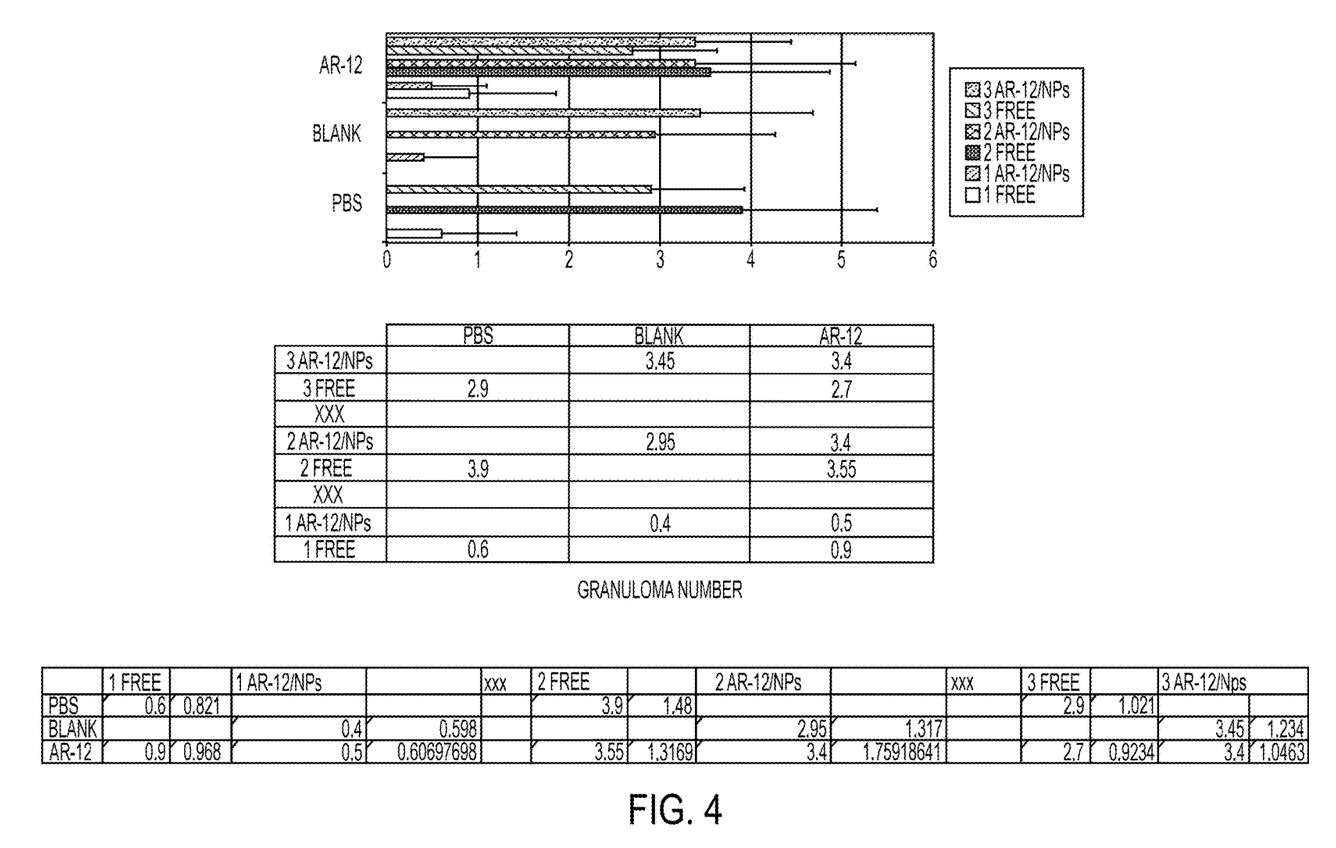
FIG. 4 provides an exemplary analysis of granulomas in BALB/c mice infected with amastigotes by tail vein injections and treated with AR-12 at day 14 and day 21 post infection.

In the experiments described in FIG. 4, the average number of grade 1-3 granulomas in the liver of BALB/c mice infected with $1\times10^7$ amastigotes by tail vein injections are shown. The mice received treatment at day 14 and day 21 post infection. AR-12 was given at a dose of 6.4 µg/mg (38.4 µg /mouse). Mice were sacrificed at Day 28 (7 days post $2^{nd}$ treatment) and the presence of granulomas from histology samples was evaluated by a board certified pathologist. Calculated scores were determined based on analysis of ten separated fields of view imaged at 40× to demonstrate distribution. (1—No cellular response; 2—Developing granuloma (initial influx of lymphocytes and monocytes, amastigotes present); 3—Mature granuloma ("functional" granuloma, parasite free); 4—Parasite free granuloma ("involuting epithelioid granuloma devoid of amastigotes); 5—Parasite free tissue without granulomas. No grade 4 or 5 granulomas were observed in any of the samples).

Figure 5:
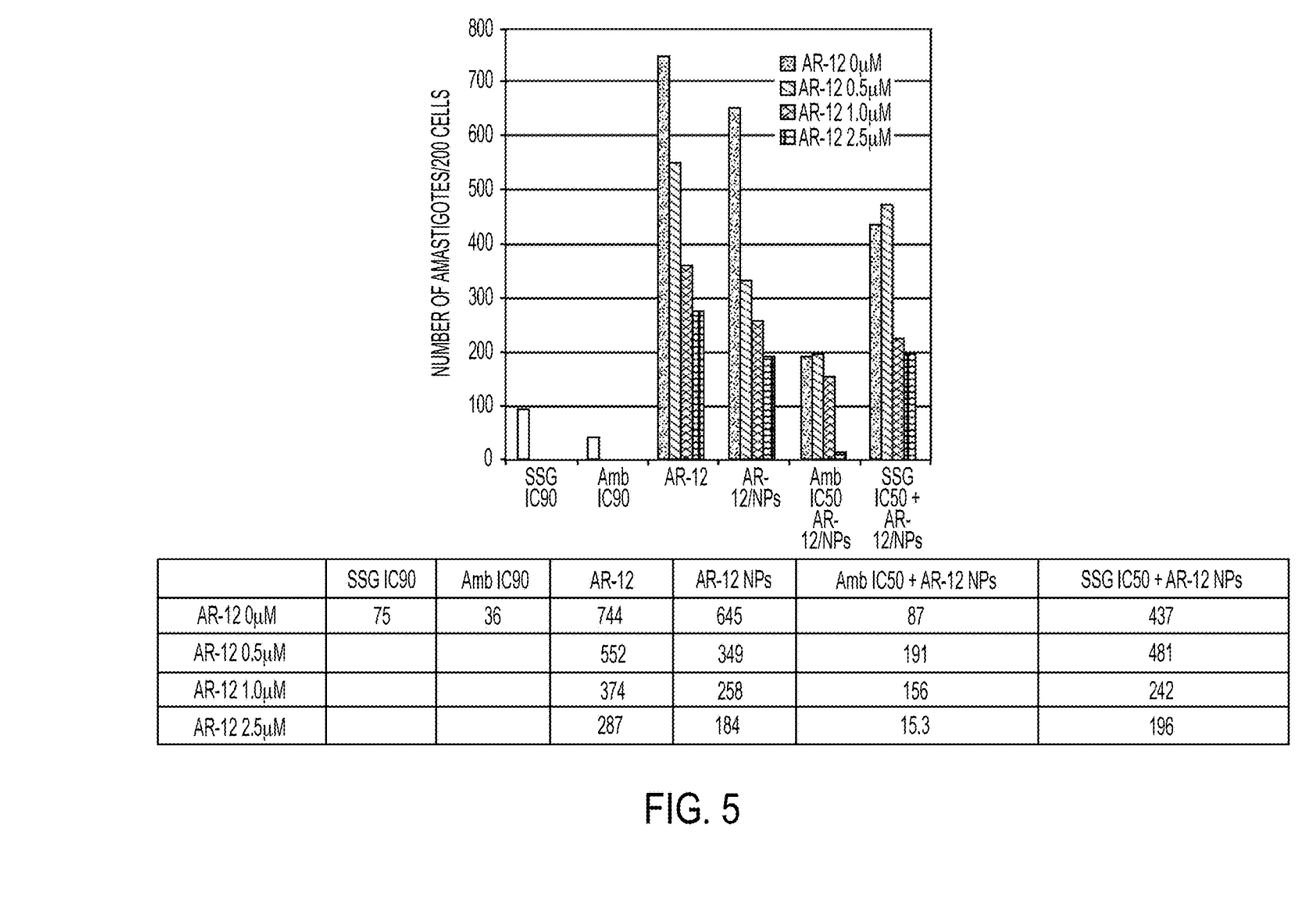
FIG. 5 depicts an exemplary in vitro evaluation of AR-12 co-delivered with amphotericin B (Amb) or sodium stibogluconate (SSG) for the treatment of *L. donovani* infected mouse bone marrow derived macrophages.

FIG. 5 provides the results of an exemplary in vitro evaluation of AR-12 co-delivered with amphotericin B (Amb) or sodium stibogluconate (SSG) for the treatment of *L. donovani* infected mouse bone marrow derived macrophages. Counts were performed 72 hours post infection. The combination of nanoparticle-encapsulated AR-12 at 2.5 µM and Amb reduced the number of amastigotes by more than 50%.

Figure 6:
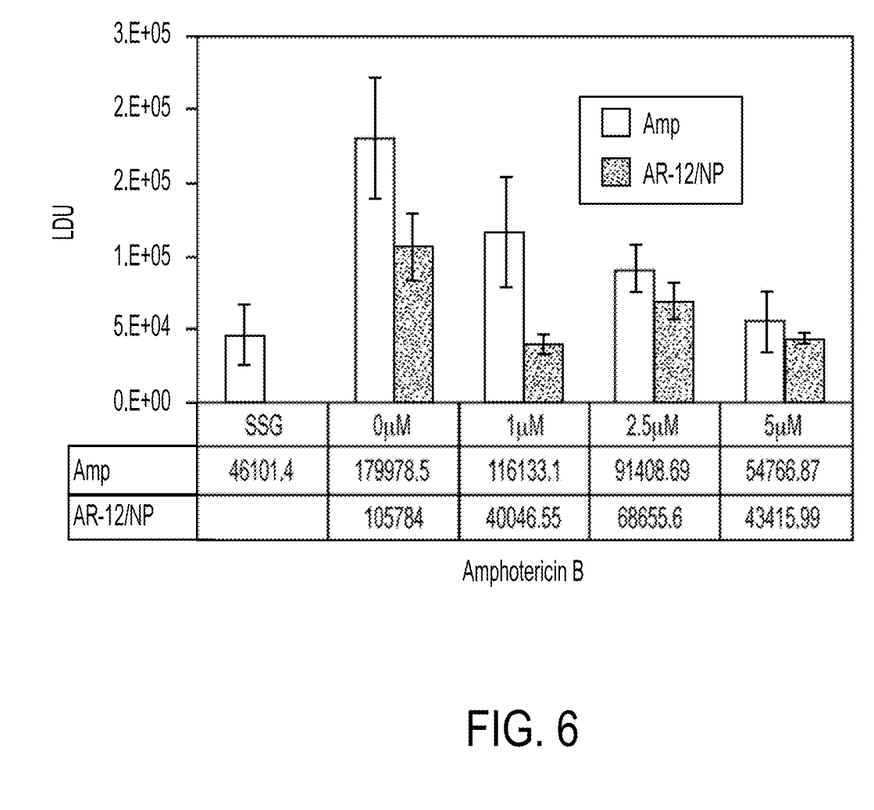
FIG. 6 shows the results of an exemplary in vivo evaluation of AR-12 in combination with amphotericin B (colloidal form) in the spleen.

FIG. 6 provides the results of an exemplary in vivo evaluation of AR-12 in combination with amphotericin B (colloidal form) in the spleen. BALB/c mice were infected with 1×10$^7$ amastigotes by tail vein injections and mice were given treatment at day 14 and day 21 post infection, i.v. AR-12 was given at 6.4 µg/mg (38.4 µg/mouse). Mice were sacrificed at Day 28 (7 days post $2^{nd}$ treatment) and parasite load was analyzed via histology and light microscopy for Leishman-Donovan units (LDU) which represents amastigote number per 1,000 host cell nuclei x organ weight (in grams) (n=5). In this aspect, the combination of nanoparticle-encapsulated (NP) AR-12 and Amp was significantly more effective that Amp alone, and AR-12/NP at 1µM in combination with Amp was more effective than SSG alone.

Figure 7:
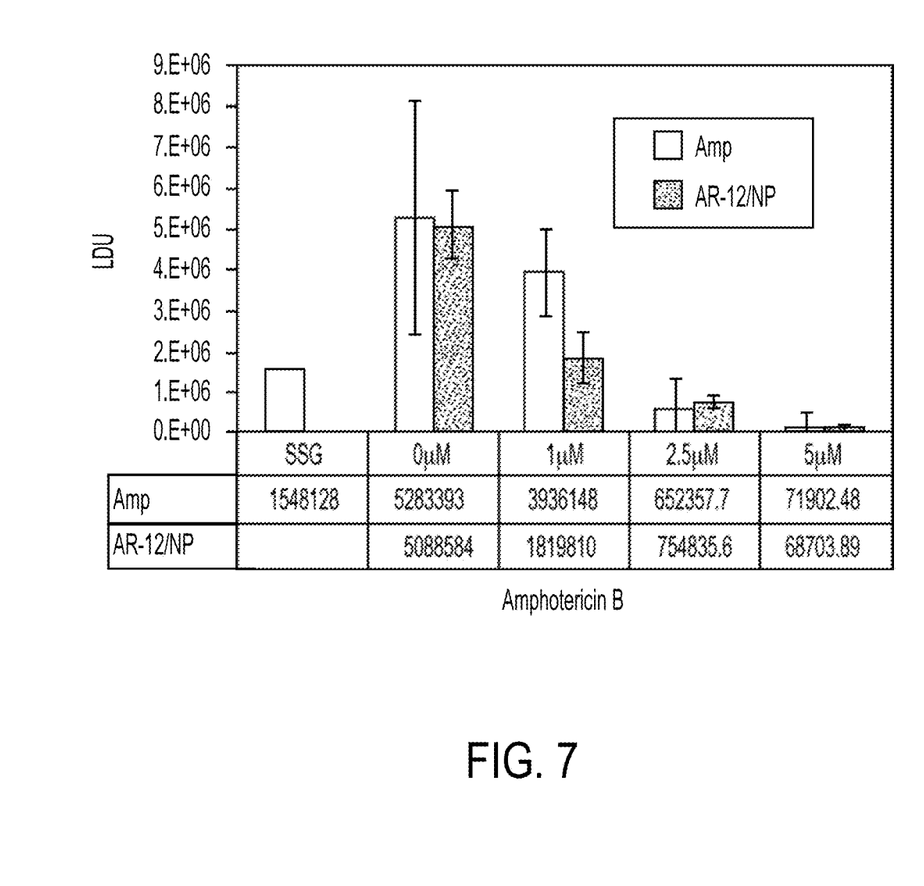
FIG. 7 shows the results of an exemplary in vivo evaluation of AR-12 in combination with amphotericin B (colloidal form) in the liver.

FIG. 7 provides the results of an exemplary in vivo evaluation of AR-12 in combination with amphotericin B (colloidal form) in the liver. BALB/c mice were infected with 1×10$^7$ amastigotes by tail vein injections and mice were given treatment at day 14 and day 21post infection, i.v. AR-12 was given at 6.4 µg/mg (38.4 µg/mouse). Mice were sacrificed at Day 28 (7 days post $2^{nd}$ treatment) and parasite load was analyzed via histology and light microscopy for Leishman-Donovan units (LDU) which represents amastigote number per 1,000 host cell nuclei×organ weight (in grams) (n=5). In this aspect, the combination of AR-12/NP and Amp was more effective than SSG alone at an AR-12 concentration of 2.5 µM or higher.

Figure 8:
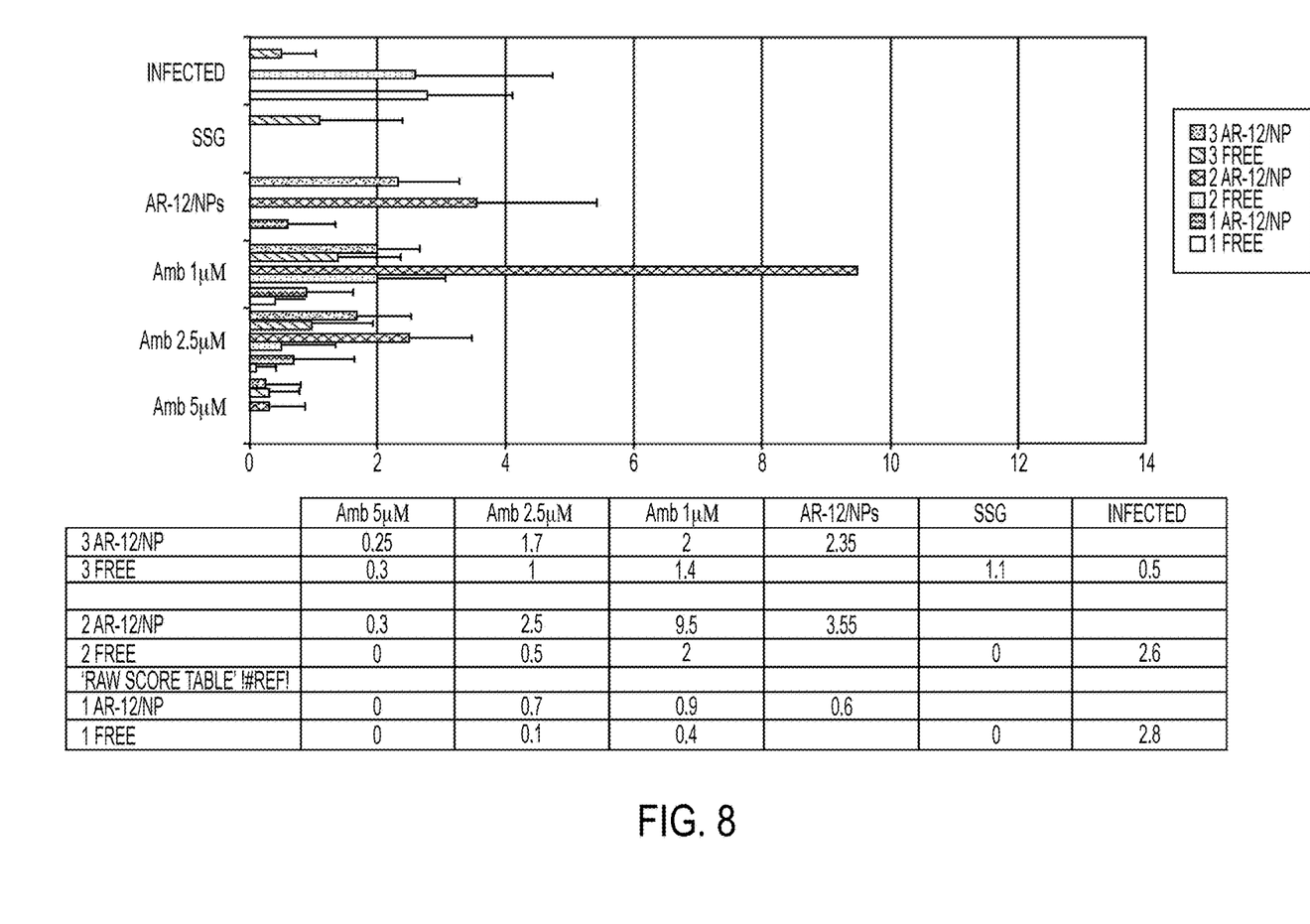
FIG. 8 provides an exemplary analysis of granulomas in BALB/c mice infected with amastigotes by tail vein injections and treated with AR-12 and SSG at day 14 and day 21 post infection.

In the experiment shown in FIG. 8, the average number of grade 1-3 granulomas in the liver of BALB/c mice are shown. In this example, mice were infected with 1×10$^7$ amastigotes by tail vein injections and given treatment at day 14 and day 21 post infection. AR-12 was administered to the mice at 6.4 µg/mg (38.4 µg/mouse). Mice were sacrificed at Day 28 (7 days post $2^{nd}$ treatment) and granuloma was evaluated by a board certified pathologist from histology samples. Calculated score determined based on analysis of 10× and 40× fields to demonstrate distribution. 1—No cellular response; 2—Developing granuloma (initial influx of lymphocytes and monocytes, amastigotes present); 3—Mature granuloma ("functional" granuloma, parasite free); 4—Parasite free granuloma ("involuting epithelioid granuloma devoid of amastigotes); 5—Parasite free tissue without granulomas. No grade 4 or 5 granulomas were observed in any of the samples.

In one aspect, AR-12 inhibits parasite growth in vitro in macrophages, indicating a host mediated effect. In another aspect, AR-12, in vivo, significantly limits parasite growth and this inhibition of growth can be increased with the co-delivery of amphotericin B.

Not every element described herein is required. Indeed, a person of skill in the art will find numerous additional uses of and variations to the methods described herein, which the inventors intend to be limited only by the claims. All references cited herein are incorporated by reference in their entirety.

What is claimed as new and desired to be protected by Letters Patent of the United States is:

1. A method of reducing the Leishman-Donovan units (LDU) of Leishmaniasis in a host, comprising: administering a daily dose of at least about 0.1 mg/kg of an autophagy inducer (AI) to the host wherein the AI is AR-12 (2-amino-N-(4-(5-(phenanthren-2-yl)-3-(trifluoromethyl)-1H-pyrazol-1-yl)phenyl)acetamide) and is co-administered with a second compound, and the Leishman-Donovan units (LDU) of Leishmaniasis in the host of Leishmaniasis are reduced.

2. The method of claim 1, wherein the Leishman-Donovan units (LDU) are reduced to less than about 47% of the untreated control.

3. The method of claim 1, wherein the second compound is selected from the group consisting of sodium stibogluconate (SSG), amphotericin B, pentamidine isethionate, miltefosine, ketoconazole, itraconazole, and fluconazole.

4. The method of claim 3, wherein the resulting Leishman-Donovan units (LDU) is less than about 1% of the untreated control.

5. A method of treating a host infected with Leishmaniasis, comprising: administering a daily dose of at least about 0.1 mg/kg of an autophagy inducer (AI) and a second compound to the host, wherein the AI is AR-12 (2-amino-N-(4-(5-(phenanthren-2-yl)-3-(trifluoromethyl)-1H-pyrazol-1-yl)phenyl)acetamide).

6. The method of claim 5, wherein the second compound is selected from the group consisting of sodium stibogluconate (SSG), amphotericin B, pentamidine isethionate, miltefosine, ketoconazole, itraconazole, and fluconazole.

* * * * *